(12) United States Patent
Funatogawa (10) Patent No.: US 6,436,034 B1
(45) Date of Patent: Aug. 20, 2002

(54) INTRABUCCAL STRETCHER (76) Inventor: Hiroyuki Funatogawa, c/o Dokuta Eru Kabushiki Kaisya 3208-1, Tori 5-Chome, Asikaga-city, Tochigi-Pref. (JP)

( * ) Notice: Subject to any disclaimer, the term of this patent is extended or adjusted under 35 U.S.C. 154(b) by 0 days.

(21) Appl. No.: 09/379,466

(22) Filed: Aug. 24, 1999

(30) Foreign Application Priority Data

Aug. 31, 1998 (JP) ............................................ 10-260949

(51) Int. Cl.[7] ................................................. A61B 1/32
(52) U.S. Cl. ...................... 600/238; 600/239; 600/243; 433/7; 433/140
(58) Field of Search ................................. 600/237, 238, 600/242, 243, 244; 433/7, 140

(56) References Cited

U.S. PATENT DOCUMENTS

| | | | |
|---|---|---|---|
| 404,652 A | * | 6/1889 | Palmer |
| 776,302 A | * | 11/1904 | Crockett |
| 1,067,572 A | * | 7/1913 | Abbott |
| 1,389,436 A | * | 8/1921 | Cameron |
| 1,450,419 A | * | 4/1923 | Heidbrink |
| 1,773,588 A | * | 8/1930 | Linde |
| 2,651,300 A | * | 9/1953 | Fehrman ........................ 128/19 |
| 3,241,550 A | * | 3/1966 | Gelarie ......................... 128/12 |
| 3,916,880 A | * | 11/1975 | Schroer ........................ 128/12 |
| 3,938,508 A | * | 2/1976 | Buckner .................... 128/76 R |
| 4,200,089 A | * | 4/1980 | Inoue ........................... 128/12 |
| 4,356,821 A | * | 11/1982 | Rind ...................... 128/207.14 |
| 4,408,989 A | * | 10/1983 | Cleary ............................ 433/7 |

* cited by examiner

Primary Examiner—John G. Weiss
Assistant Examiner—Mital Patel
(74) Attorney, Agent, or Firm—Lorusso & Loud (57) ABSTRACT

Disclosed is an intrabuccal stretcher having essentially a supporting bar and a pushing part formed at each distal end of the supporting bar; the pushing parts having such a thickness and such a roundish shape as are suitable for pushing internal sides of buccae; the supporting bar being bent symmetrically with respect to the vertical axis; the pushing parts being extended outward from the distal ends of the supporting bar; wherein the pushing par-n are inserted into an oral cavity with the supporting bar remaining partly outside the oral cavity to push and simulate internal sides of the buccae.

5 Claims, 6 Drawing Sheets

FIG. 18

INTRABUCCAL STRETCHER

BACKGROUND OF THE INVENTION

The present invention relates generally to a device for stretching muscles and tendons related to bucca, particularly to an intrabuccal stretcher which is a device having a specific shape and which is inserted to an oral cavity to stretch internal sides of buccae so as to activate muscles and tendons related to bucca, in turn, to achieve reinforcement of jaw bones and gums and activation of salivary glands.

DESCRIPTION OF THE RELATED ART

Buccae have many intricate functions in our daily lives. For example, they help respiration, eating and drinking, phonation and produce delicate expressions of the face in cooperation with the mouth. However, there are not a few in the elderly who have difficulty in masticating and swallowing food, while weakening of buccal muscles and jaw muscles which lead to retrogression of jaw bones is frequently observed in the younger generations today, and these phenomena are giving rise to serious social problems Under such circumstances, exercise of the tongue to stimulate salivary glands and accelerate secretion and external buccal massage using fingers are becoming popular as easy oral hygiene.

SUMMARY OF THE INVENTION

The present invention relates to a stretcher and reinforcing device developed with a view to preventing weakening of buccal muscles, jaw muscles and other muscles related to them and to improving such muscles.

In order to attain the above objective, the present invention provides an intrabuccal stretcher having a supporting bar and a pushing part formed at each distal end of the supporting bar; the pushing part having such a thickness and such a roundish shape as are suitable for pushing internal sides of buccae; the supporting bar being bent almost symmetrically with respect to the vertical axis; the pushing parts being extended outward from the distal ends of the supporting bar; wherein the pushing parts are inserted into an oral cavity with the supporting bar remaining partly outside the oral cavity to push and stimulate internal sides of the buccae.

Other aspects and advantages of the invention will become apparent from the following description, taken in conjunction with the accompanying drawings illustrated by way of examples the principles of the invention.

BRIEF DESCRIPTION OF THE DRAWINGS

The invention together with the objects and advantages thereof, may best be understood by reference to the following description of the presently preferred embodiments together with the accompanying drawings in which.

DETAILED DESCRIPTION OF THE PREFERRED EMBODIMENTS

Figure 1:
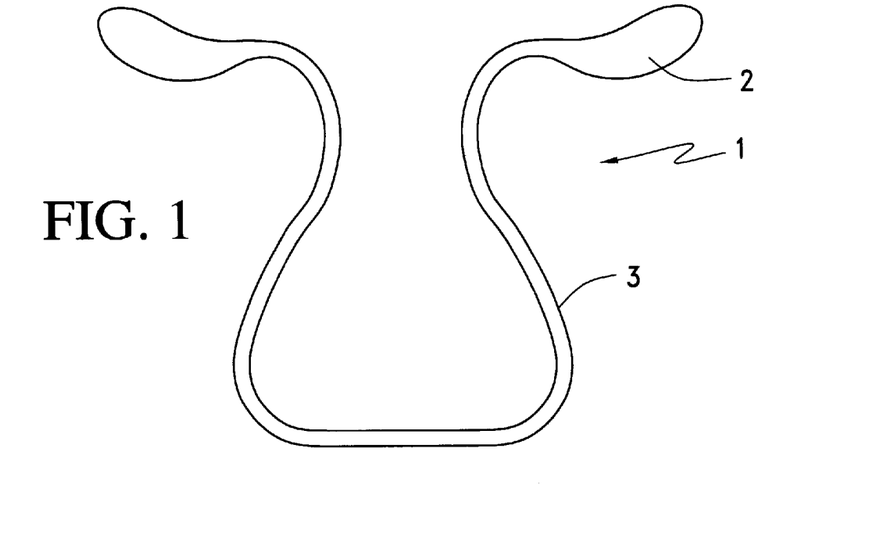
FIG. 1 is a front view showing an intrabuccal stretcher according to a first embodiment of the present invention.
Figure 2:
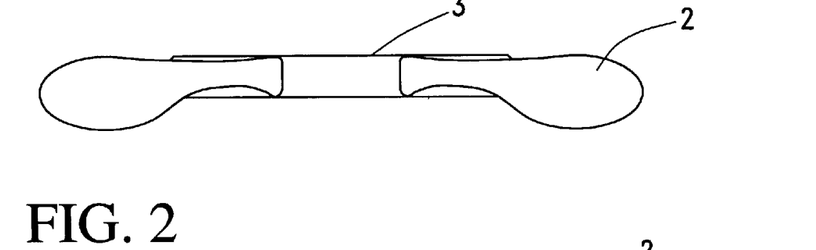
FIG. 2 is a plan view of the intrabuccal stretcher according to the first embodiment.

The mode for carrying out the present invention will be described together with the examples shown in the drawings. FIG. 1 is a front view of an intrabuccal stretcher according to a first embodiment, and FIG. 2 is a plan view of the same. she intrabuccal stretcher 1 shown in FIG. 1 consists essentially of a pair of pushing parts 2 and a supporting bar 3.

Figure 3:
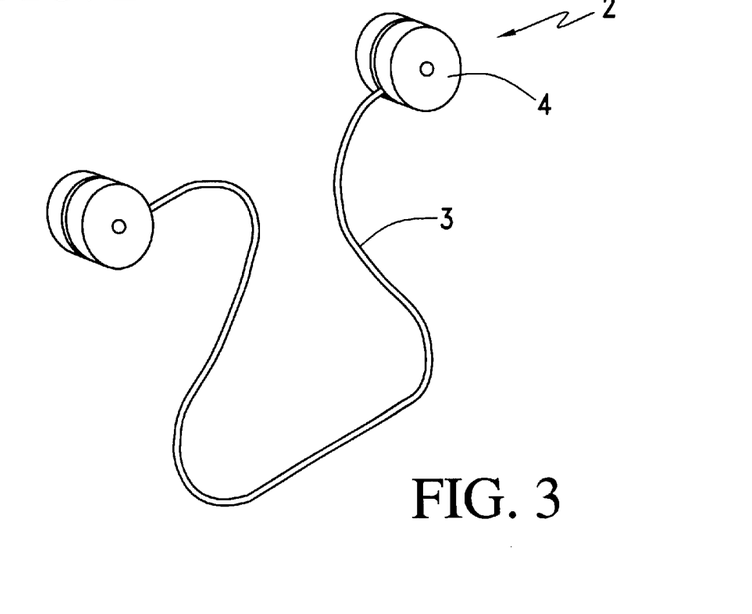
FIG. 3 is an explanatory drawing showing the case where the pressing parts are rollers.

The pushing parts 2, which are formed at both distal ends of the supporting bar 3, have such a thickness and such a roundish shape as are suitable for pushing in an oral cavity the internal sides of the buccae. While the pushing parts 2 and the supporting bar 3 are formed integrally in the illustrated example, the intrabuccal stretcher 1 may have additional parts. FIG. 3 shows such an example, in which a pair of rollers 4 are used as the pushing parts 2.

The lower side at the distal end portion of each pushing part 2 shown in FIG. 1, i.e., the portion to be abutted directly against the internal side of the bucca, has a curved surface which is rounded gently. Thus, the pushing parts 2 can be brought into mild contact with the internal sides of the buccae when the span between the pushing parts 2 is widened by pulling them outward, and one can use the intrabuccal stretcher 1 without pain in the buccal cavity.

The supporting bar 3, which is substantially U-shaped and is curved almost symmetrically with respect to the vertical axis, as shown in FIG. 1, is bent further at each distal end to form the pushing part 2. It should be noted here that in order to facilitate insertion of the pushing parts 2 into the oral cavity, the supporting bar 3 is allowed to have a bent configuration such that it is retracted immediately before each pushing part 2 to adjust the clearance between the pushing parts 2.

Figure 4:
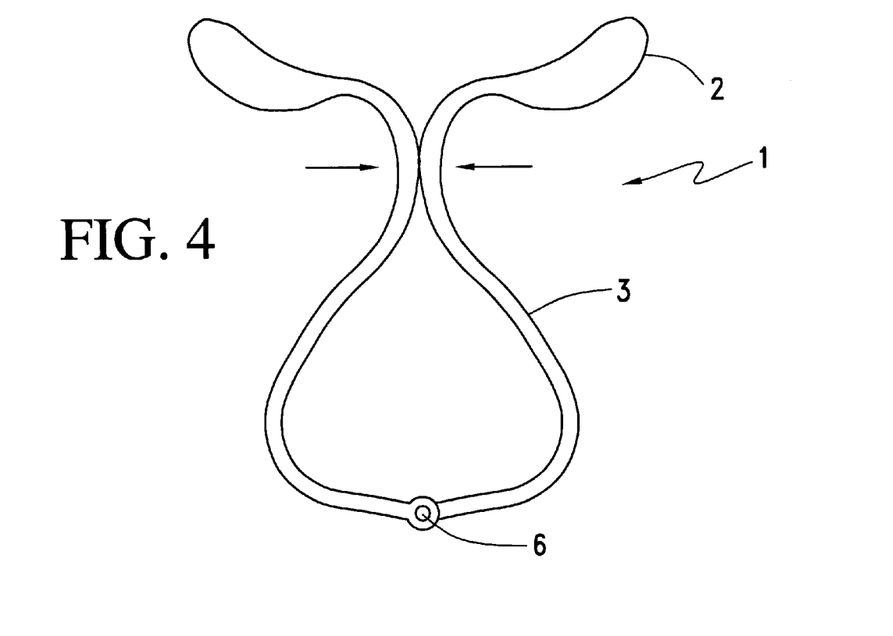
FIG. 4 is a front view showing an intrabuccal stretcher according to a second embodiment of the present invention.
Figure 5:
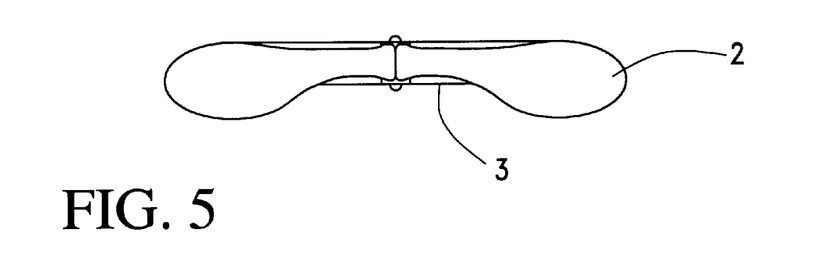
FIG. 5 is a plan view of the intrabuccal stretcher according to the second embodiment.

While there may be given some considerable means for adjusting the clearance between the pushing parts 2, one is realized in an intrabuccal stretcher 1 according to a second embodiment as shown in the front view of FIG. 4 and in the plan view of FIG. 5. The supporting bar 3 is separated at the bottom center into two parts, i.e., a right half and a left half. The proximal end portions of the thus separated supporting bars 3 are pivotally and lockably connected to each other by a pin 6. The example Illustrated in FIGS. 4 and 5 shows the state where the intrabuccal stretcher 1 is locked with the minimum width.

Figure 8:
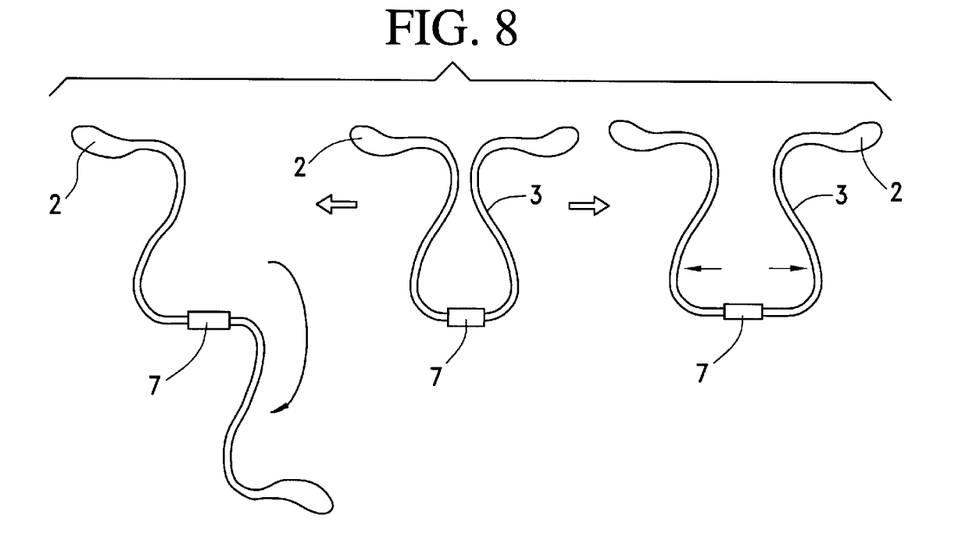
FIG. 8 is a drawing explaining actions of an intrabuccal stretcher having a width-adjusting ring.

As second width-adjusting means, there is a case employing a width-adjusting ring 7 shown in FIG. 8. The supporting bar 3 shown in FIG. 8 is separated at the bottom center into two parts, i.e., a right half and a left half. The proximal end portions of the thus separated supporting bars 3 are closably connected to each other by the width-adjusting ring 7. The middle illustration in FIG. 8 is of the basic form, and a wide intrabuccal stretcher 1 can be obtained by loosening the width-adjusting ring 7 in the basic form to pull the supporting bars 3 outward and fastening the bars 3 at a desired position with the width-adjusting ring 7.

Further, as shown in the left illustration in FIG. 8, a single intrabuccal stretcher 1 can be obtained if the supporting bars 3 are fastened and locked with one supporting bar 3 being pivoted down after loosening of the width-adjusting ring 7.

Figure 6:
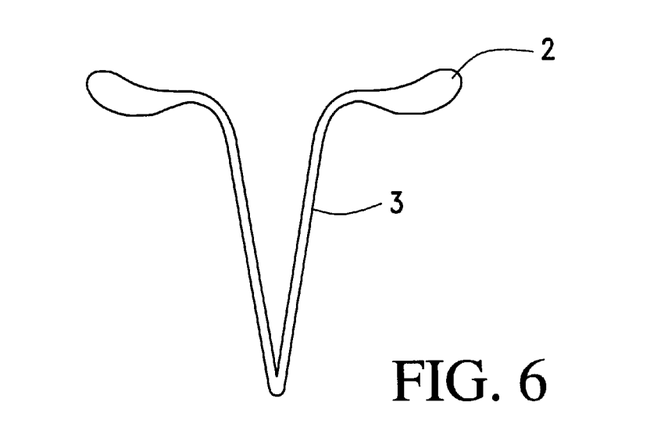
FIG. 6 is a front view of an intrabuccal stretcher in which the supporting bar is bent into a V-shape.
Figure 7:
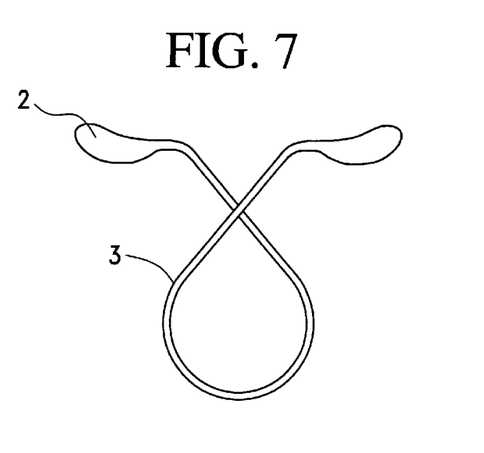
FIG. 7 is a front view of an intrabuccal stretcher in which the supporting bar is crossed.

The configuration of the supporting bar 3 may not be limited to that shown in FIG. 1, but there may be considered various configurations including the V-shape as shown in FIG. 6, the crossed shape in which the supporting bar 3 is crossed near distal end portions as shown in FIG. 7, as well as, a vertically oblong rectangular shape and a rectangular shape reducing toward its top (which are not shown).

The supporting bar 3 is preferably made of a flexible material, and the material is not critical and may be a spring or a resin so long as it has flexibility.

Figure 10:
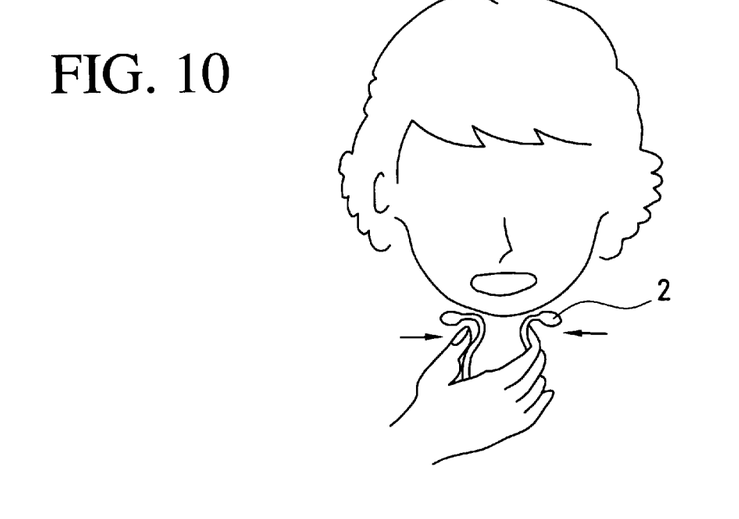
FIG. 10 is an explanatory drawing when the intrabuccal stretcher is squeezed to be inserted into the oral cavity.
Figure 11:
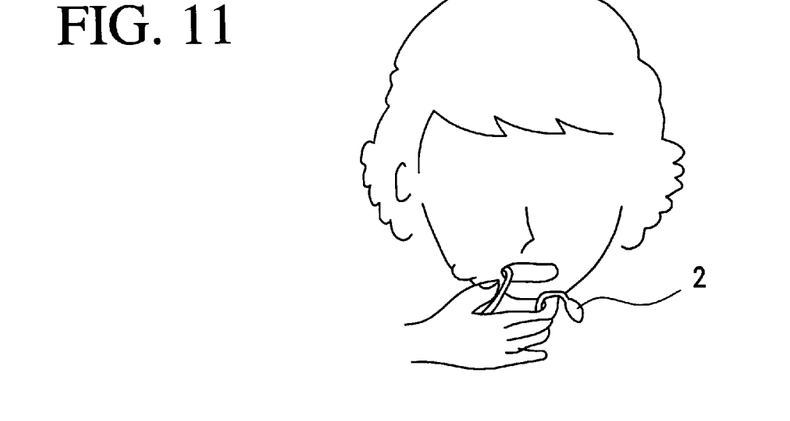
FIG. 11 is an explanatory drawing when the pushing parts of the intrabuccal stretcher are inserted into the oral cavity separately.
Figure 12:
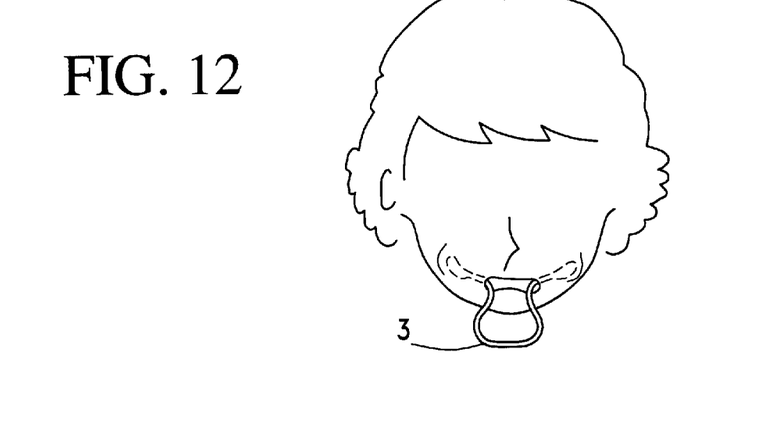
FIG. 12 is an explanatory drawing showing the state where the intrabuccal stretcher is already inserted into the buccal cavity.

FIGS. 10 to 12 are explanatory drawings when the intrabuccal stretcher 1 shown in FIG. 1 is inserted to an oral cavity. As shown in FIG. 12, when the pushing parts 2 of the intrabuccal stretcher 1 are to be inserted into the oral cavity, the supporting bar 3 of the intrabuccal stretcher 1 is squeezed inward for insertion, as shown in FIG. 10 or are inserted one by one as shown in FIG. 11.

Figure 13:
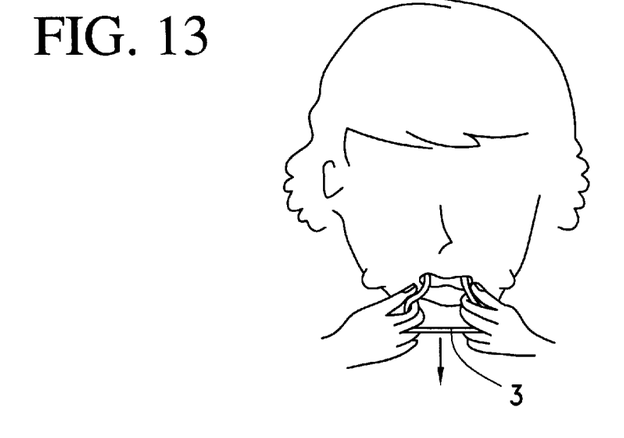
FIG. 13 is an explanatory drawing showing the state where the intrabuccal stretcher is pulled forward.
Figure 14:
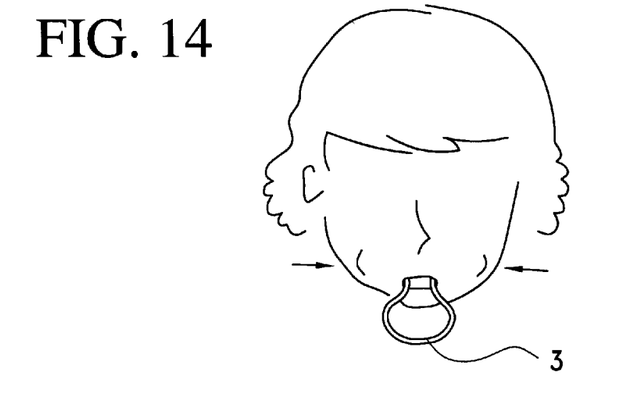
FIG. 14 is an explanatory drawing showing the state of stretching caused by the action of the mouth.
Figure 15:
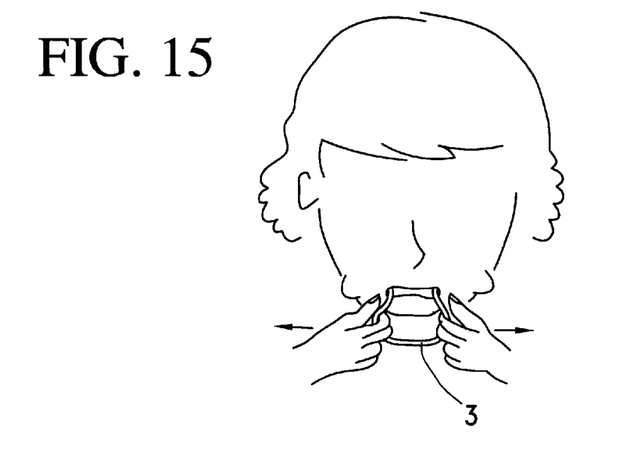
FIG. 15 is an explanatory drawing showing the state where the buccae are stretched by widening the intrabuccal stretcher.
Figure 16:
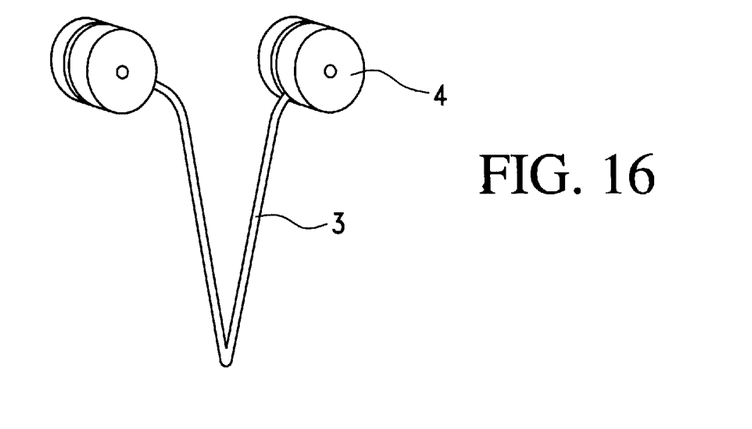
FIG. 16 is another embodiment of the intrabuccal stretcher in which the supporting bar is V-shaped.
Figure 17:
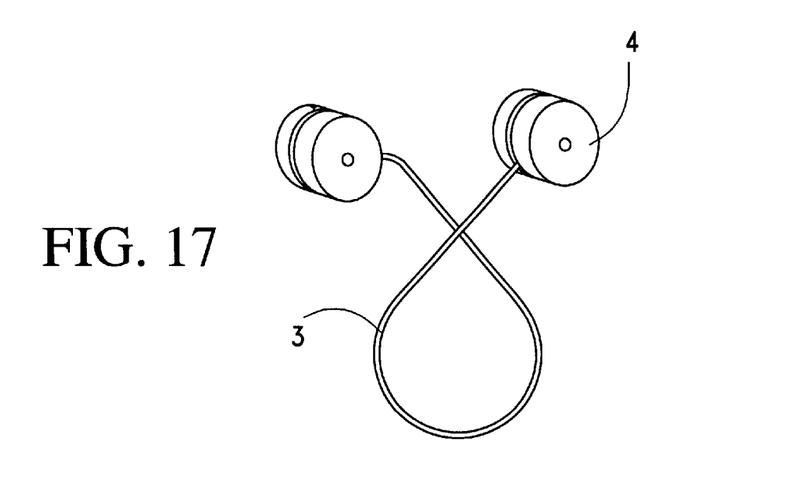
FIG. 17 is a front view of another embodiment of the intrabuccal stretcher in which the supporting bar is crossed.
Figure 18:
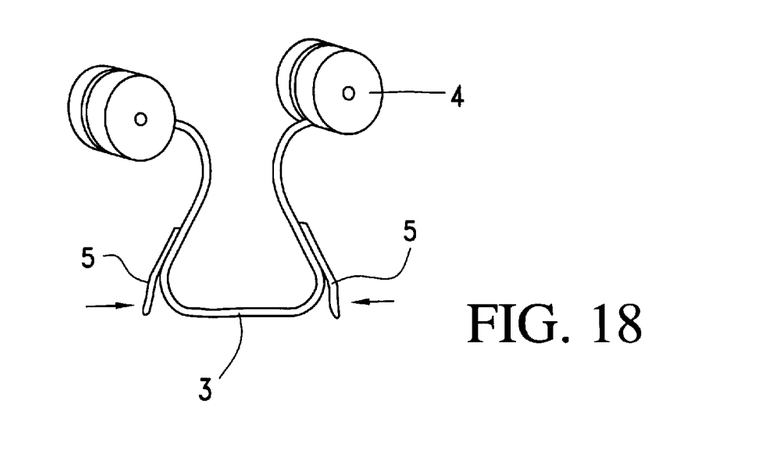
FIG. 18 is a front view of the intrabuccal stretcher of the present invention having added levers.

FIGS. 13 to 15 are explanatory drawings showing states where buccae are stretched by the intrabuccal stretcher. To describe basics of the usage of the intrabuccal stretcher 1, after the intrabuccal stretcher 1 is inserted to the oral cavity as described above, it is pulled forward, shifted sideways or widened with the fingers to stretch the internal sides of the buccae.

FIG. 13 shows an example where the internal sides of the buccae are stretched depthwise by pulling forward the supporting bar 3 as indicated by the arrow in the drawing. FIGS. 14 and 15 show examples where the internal sides of the buccae are stretched laterally. In FIG. 14, the internal sides of the buccae are abutted against the pushing parts 2 and are tightened by deliberate motion of the mouth to be stretched utilizing the flexibility of the supporting bar 3; whereas in FIG. 15, the supporting bars 3 are pulled outward with fingers to widen the span between the pushing parts 2 and stretch the internal sides of the buccae.

According to the above usage, both internal sides of the buccae are stretched simultaneously. However, there are considered various usage: The internal sides of the buccae may be stretched separately, or the intrabuccal stretcher 1 may be twisted to abut one pushing part 2 against the upper part of one bucca and the other pushing part 2 against the lower part of the other bucca.

Although not shown, it is also possible to use the intrabuccal stretcher 1 by inserting only one pushing part 2 into the oral cavity. In this case, the internal side of only one bucca can be stretched intensively.

While the span between the supporting bars 3 is usually widened by pulling them outward with fingers of both hands, if additional levers 5 are attached to the lower par of the supporting bar 3 to extend down therefrom, as shown in FIG. 10, widening of the span can be facilitated utilizing the principles of the lever and fulcrum by nipping the additional levers 5. It is also possible to automate the widening action and the width-adjusting action using a motor and the like.

The present invention exhibits the following having because of the constitution as described above:

(1) Muscles and tendons relating to the oral cavity can be massaged using the intrabuccal stretcher having a simple structure consisting essentially of a pair of pressing parts and a supporting bar;
(2) Buccae can be stretched without being hurt at the internal sides, since the pushing parts have such a thickness and such a roundish shape as are suitable for pushing the internal sides of the buccae;
(3) Since the intrabuccal stretcher is used with the supporting bar remaining partly outside the oral cavity, stretching can be carried cut by operating the supporting bar with fingers, simplifying usage of the stretcher; and
(4) The supporting bar 3 is curved almost symmetrically with respect to the vertical axis and is provided at each distal end with the pushing part, so that the internal sides of the buccae can be simultaneously stretched, effectively.

Although some embodiments of the present invention have been described herein, it should be apparent to those skilled in the art What the present invention may be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

What is claimed is:
1. An intrabuccal stretcher comprising:
   a supporting bar and a roller attached at each of distal ends of the supporting bar;
   wherein the rollers have such a thickness and such a roundish shape as are suitable for pushing internal sides of buccae;
   wherein the supporting bar is bent almost symmetrically with respect to a center thereof;
   wherein the rollers extend outward from the distal ends of the supporting bar; and
   whereby the rollers may be inserted into an oral cavity with the supporting bar remaining partly outside the oral cavity to push and stimulate internal sides of the buccae.
2. The intrabuccal stretcher according to claim 1, wherein the supporting bar is V-shaped.

3. The intrabuccal stretcher according to claim 1, wherein the supporting bar is crossed near its distal ends.

4. The intrabuccal stretcher according to claim 1, further comprising levers attached to the supporting bar.

5. An intrabuccal stretcher comprising:

a supporting bar and a pushing part formed at each of distal ends of the supporting bar;

wherein each pushing part has such a thickness and such a roundish shape as are suitable for pushing internal sides of buccae;

wherein the supporting bar is bent almost symmetrically with respect to a center thereof and is crossed near its distal end portions;

wherein the pushing parts extend outward from the distal ends of the supporting bar; and    whereby the pushing parts may be inserted into an oral cavity with the supporting bar remaining partly outside the oral cavity to push and stimulate internal sides of the buccae.

\* \* \* \* \*

UNITED STATES PATENT AND TRADEMARK OFFICE
CERTIFICATE OF CORRECTION

PATENT NO.   : 6,436,034 B1
DATED        : August 20, 2002
INVENTOR(S)  : Hiroyuki Funatogawa It is certified that error appears in the above-identified patent and that said Letters Patent is hereby corrected as shown below:

Title page,
Item [57], ABSTRACT, delete ABSTRACT and replace with new ABSTRACT:

(57) ABSTRACT

An intrabuccal stretcher has a supporting bar and a pushing part formed at each distal end of the supporting bar, the pushing parts having such a thickness and such a roundish shape as are suitable for pushing against internal sides of buccae. The supporting bar is bent symmetrically with respect to its center and the pushing parts extend outward from the distal ends of the supporting bar. The pushing parts are inserted into an oral cavity with the supporting bar remaining partly outside the oral cavity to push and stimulate internal sides of the buccae.

Delete Column 1 thru Column 4, and replace with the attached Columns 1 thru 4.

Signed and Sealed this

Eighteenth Day of November, 2003

JAMES E. ROGAN
*Director of the United States Patent and Trademark Office*

INTRABUCCAL STRETCHER

BACKGROUND OF THE INVENTION

The present invention relates generally to a device for stretching muscles and tendons related to buccae, particularly to an intrabuccal stretcher which is a device having a specific shape and which is inserted to an oral cavity to stretch buccae so as to activate muscles and tendons related to buccae and, in turn, to achieve reinforcement of jaw bones and gums and activation of salivary glands.

DESCRIPTION OF THE RELATED ART

Buccae have many intricate functions in our daily lives. For example, they help respiration, eating and drinking, phonation and produce delicate expressions of the face in cooperation with the mouth. However, there are not a few in the elderly who have difficulty in masticating and swallowing food, while weakening of buccal muscles and jaw muscles which lead to retrogression of jaw bones is frequently observed in the younger generations today, and these phenomena are giving rise to serious social problems.

Under such circumstances, exercise of the tongue to stimulate salivary glands and accelerate secretion and external buccal massage using fingers are becoming popular oral hygiene exercises.

SUMMARY OF THE INVENTION

The present invention relates to a stretcher and reinforcing device developed with a view to preventing weakening of buccal muscles, jaw muscles and other muscles related to them and to improving such muscles.

In order to attain the above objective, the present invention provides an intrabuccal stretcher having a supporting bar and a pushing part (buccal pressing portion) formed at each distal end of the supporting bar; the pushing part having such a thickness and such a roundish shape as are suitable for pushing against internal sides of buccae; the supporting bar being bent almost symmetrically with respect to the center; the pushing parts being extended outward from the distal ends of the supporting bar; wherein the pushing parts are inserted into an oral cavity with the supporting bar remaining partly outside the oral cavity to push and stimulate internal sides of the buccae.

Other aspects and advantages of the invention will become apparent from the following description, taken in conjunction with the accompanying drawings illustrated by way of examples of the invention.

BRIEF DESCRIPTION OF THE DRAWINGS

Figure 9:
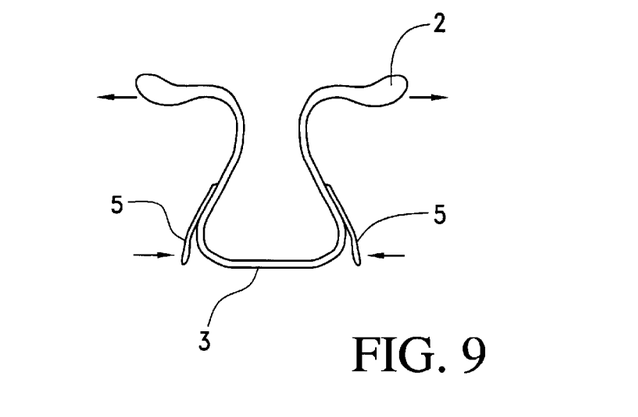
FIG. 9 is a front view of an intrabuccal stretcher having additional levers.

The invention together with the objects and advantages thereof, may best be understood by reference to the following description of the presently preferred embodiments together with the accompanying drawings in which:

FIG. 1 is a front view of an intrabuccal stretcher according to a first embodiment of the present invention;

FIG. 2 is a plan view of the intrabuccal stretcher according to the first embodiment;

FIG. 3 is a schematic view of an embodiment wherein the pressing parts are rollers;

FIG. 4 is a front view of an intrabuccal stretcher according to another embodiment of the present invention;

FIG. 5 is a plan view of the intrabuccal stretcher of the embodiment of FIG. 4;

FIG. 6 is a front view of an embodiment of an intrabuccal stretcher in which the supporting bar is bent into a V-shape;

FIG. 7 is a front view of an embodiment of an intrabuccal stretcher in which the supporting bar is crossed;

FIGS. 8 is a drawing series explaining width adjustment of an embodiment of an intrabuccal stretcher of the invention having a width-adjusting ring;

FIG. 9 is a front view of an embodiment of an intrabuccal stretcher of the present invention having added levers;

FIG. 10 is a drawing illustrating squeezing the intrabuccal stretcher for insertion into the oral cavity;

FIG. 11 is a drawing illustrating insertion of the buccal pressing portions separately into the oral cavity;

FIG. 12 is a drawing showing the intrabuccal stretcher inserted into the buccal cavity;

FIG. 13 is a drawing illustrating the exercise of pulling the intrabuccal stretcher forward;

FIG. 14 is a drawing illustrating the stretching of the mouth caused by use of the intrabuccal stretcher;

FIG. 15 is a drawing showing the buccae stretched by spreading the intrabuccal stretcher.

DETAILED DESCRIPTION OF THE PREFERRED EMBODIMENTS

FIG. 1 is a front view of an intrabuccal stretcher according to a first embodiment, and FIG. 2 is a plan view of the same. The intrabuccal stretcher 1 shown in FIG. 1 consists essentially of a pair of pushing parts 2 and a supporting bar 3.

The pushing parts 2, which are formed at both distal ends of the supporting bar 3, have such a thickness and such a roundish shape as are suitable for insertion into an oral cavity and pressing against the internal sides of the buccae. While the pushing parts 2 and the supporting bar 3 are formed integrally in the illustrated example, the intrabuccal stretcher 1 be composed of component parts. FIG. 3 shows such an embodiment, in which a pair of rollers 4 are used as the pushing parts 2.

The lower side of the distal end portion of each pushing part 2 shown in FIG. 1, i.e., the portion which abuts directly against the internal side of the bucca, has a curved surface which is gently rounded. Thus, the pushing parts 2 can be brought into mild contact with the internal sides of the buccae when the span between the pushing parts 2 is widened by pulling them outward (FIG. 15), and one can use the intrabuccal stretcher 1 without pain in the buccal cavity.

The supporting bar 3, which is substantially U-shaped and is curved almost symmetrically with respect to its center, as shown in FIG. 1, is bent further at each distal end to form the pushing part 2. It should be noted here that in order to facilitate insertion of the pushing parts 2 into the oral cavity, the supporting bar 3 is provided with a bent configuration to allow adjustment of the clearance between the pushing parts 2.

While various means can be adopted for adjusting the clearance between the pushing parts 2, one such means is realized in an intrabuccal stretcher 1 according to the embodiment shown in FIG. 4 and FIG. 5. The supporting bar 3 is separated at the bottom center into two parts, i.e., a right half and a left half. The proximal end portions of the thus separated supporting bars 3 are pivotally and lockably connected to each other by a pin 6. The example illustrated in FIGS. 4 and 5 shows the state where the intrabuccal stretcher 1 is locked with the minimum width.

A second width-adjusting means is the width-adjusting ring 7 shown in FIG. 8. The supporting bar 3 shown in FIG.

8 is separated at the bottom center into two parts, i.e., a right half and a left half. The proximal end portions of the thus separated supporting bars 3 are closably connected to each other by the width-adjusting ring 7. The middle illustration in FIG. 8 is of the basic form, and a wide intrabuccal stretcher 1 can be obtained by loosening the width-adjusting ring 7 to allow the supporting bars 3 to be pulled outward and then fastened at a desired position with the width-adjusting ring 7.

Further, as shown in the left illustration in FIG. 8, a single intrabuccal stretcher 1 can be obtained if the supporting bars 3 are fastened and locked with one supporting bar 3 being pivoted down after loosening of the width-adjusting ring 7.

The configuration of the supporting bar 3 is not limited to that shown in FIG. 1 but, rather, may be any of various configurations including the V-shape as shown in FIG. 6, the crossed shape in which the supporting bar 3 is crossed near distal end portions as shown in FIG. 7, as well as, a vertically oblong rectangular shape and a rectangular shape reducing toward its top (which are not shown).

The supporting bar 3 is preferably made of a flexible material, and the material is not critical and may be a spring or a resin so long as it has flexibility.

FIGS. 10 to 12 are explanatory drawings explaining insertion of the intrabuccal stretcher 1 shown in FIG. 1 into an oral cavity. As shown in FIG. 12, when the pushing parts 2 of the intrabuccal stretcher 1 are to be inserted into the oral cavity, the supporting bar 3 of the intrabuccal stretcher 1 is squeezed inward for insertion, as shown in FIG. 10 or the pushing parts 2 are inserted one by one as shown in FIG. 11.

FIGS. 13 to 15 illustrate stretching of the buccae by the intrabuccal stretcher. In the basic usage of the intrabuccal stretcher 1, after the intrabuccal stretcher I is inserted to the oral cavity as described above, it is pulled forward, shifted sideways or widened with the fingers to stretch the buccae.

FIG. 13 shows an example where the buccae are stretched by pulling forward the supporting bar 3 as indicated by the arrow in the drawing. FIGS. 14 and 15 show examples where the buccae are stretched laterally. In FIG. 14, the buccae are pressed by the pushing parts 2 and are tightened by deliberate motion of the mouth for stretching utilizing the flexibility of the supporting bar 3; whereas in FIG. 15, the supporting bars 3 are pulled outward with fingers to widen the span between the pushing parts 2 and thereby stretch the buccae.

According to the above usage, both the buccae are stretched simultaneously. However, there are various other usages. The buccae may be stretched separately, or the intrabuccal stretcher 1 may be twisted to abut one pushing part 2 against the upper part of one bucca and the other pushing part 2 against the lower part of the other bucca.

Although not shown, it is also possible to use the intrabuccal stretcher 1 by inserting only one pushing part 2 into the oral cavity. In this case, one bucca only can be stretched intensively.

While the span between the supporting bars 3 is usually widened by pulling them outward with fingers of both hands, if levers 5 are attached to the lower part of the supporting bar 3 to extend down therefrom, as shown in FIG. 10, widening of the span can be facilitated utilizing the principles of the lever and fulcrum by nipping the levers 5. It is also possible to automate the widening action and the width adjusting action using a motor and the like.

The present invention provides the following effects:
(1) Muscles and tendons of the oral cavity can be massaged using the intrabuccal stretcher having a simple structure consisting essentially of a pair of pressing parts and a supporting bar;
(2) Buccae can be stretched without injury to their internal sides, since the pushing parts have such a thickness and such a roundish shape as are suitable for pushing against the internal sides of the buccae;
(3) Since the intrabuccal stretcher is used with the supporting bar remaining partly outside the oral cavity, stretching can be carried out by operating the supporting bar with fingers, simplifying usage of the stretcher; and
(4) The supporting bar 3 is curved almost symmetrically with respect to its center and is provided at each distal end with the pushing part, so that the buccae can be simultaneously stretched, effectively.

Although some embodiments of the present invention have been described herein, it should be apparent to those skilled in the art that the present invention may be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

What is claimed is:

1. An intrabuccal stretcher comprising:
   a supporting bar and a roller attached at each of distal ends of the supporting bar;
   wherein the rollers have such a thickness and such a roundish shape as are suitable for pushing internal sides of buccae;
   wherein the supporting bar is bent almost symmetrically with respect to a center thereof;
   wherein the rollers extend outward from the distal ends of the supporting bar; and
   whereby the rollers may be inserted into an oral cavity with the supporting bar remaining partly outside the oral cavity to push and stimulate internal sides of the buccae.

2. The intrabuccal stretcher according to claim 1, wherein the supporting bas is V-shaped.

3. The intrabuccal stretcher according to claim 1, wherein the supporting bar is crossed near its distal ends.

4. The intrabuccal stretcher according to claim 1, further comprising levers attached to the supporting bar.

5. An intrabuccal stretcher comprising:
   a supporting bar and a pushing part formed at each of distal ends of the supporting bar;
   wherein each pushing part has such a thickness and such a roundish shape as are suitable for pushing internal sides of buccae;
   wherein the supporting bar is bent almost symmetrically with respect to a center thereof and is crossed near its distal end portions;
   wherein the pushing parts extend outward from the distal ends of the supporting bar; and
   whereby the pushing parts may be inserted into an oral cavity with the supporting bar remaining partly outside the oral cavity to push and stimulate internal sides of the buccae.

* * * * *